United States Patent [19]

Lee

[11] Patent Number: 4,510,151

[45] Date of Patent: Apr. 9, 1985

[54] PYRIDINYLIMIDAZOLE PHARMACEUTICAL COMPOSITION

[75] Inventor: Thomas D. Lee, Scarsdale, N.Y.

[73] Assignee: USV Pharmaceutical Corporation, Tarrytown, N.Y.

[21] Appl. No.: 578,918

[22] Filed: Feb. 10, 1984

[51] Int. Cl.$^3$ .............................................. A61K 31/44
[52] U.S. Cl. .................................................... 514/341
[58] Field of Search ......................................... 424/263

[56] References Cited

U.S. PATENT DOCUMENTS 4,302,464 11/1981 LaMattina et al. ................. 424/263

OTHER PUBLICATIONS

LaMattina, "The Synthesis of 2-Amino-4-(-4-imidazolyl)pyridines" Journal of Heterocyclic Chemistry 20, 533–538, (1983).

Murakami et al., "An Efficient Synthesis of 5-Diethoxymethylimidazole-4-carboxylate, A Potential Precursor for Various Imidazole Derivatives", Tetrahedron Letters, 23(45), pp. 4729–4732, (1982).

Primary Examiner—Albert T. Meyers
Assistant Examiner—Joyce L. Morrison

[57] ABSTRACT

A pharmaceutical composition containing a therapeutically effective amount of a pyridinylimidazole 4- or 5-substituted carboxylic acid and esters thereof is provided to treat cardiovascular ailment.

5 Claims, No Drawings

PYRIDINYLIMIDAZOLE PHARMACEUTICAL COMPOSITION

FIELD OF INVENTION

The present invention relates to a pharmaceutical composition containing a therapeutically effective amount of a pyridinylimidazole 4- or 5-substituted carboxylic acid and esters thereof used in the treatment of cardiovascular ailments.

DESCRIPTION OF THE PRIOR ART

There is a constant search by investigators in the field of organic medicinal chemistry to find compositions, readily and economically prepared, which effectively treat cardiovascular ailments such as congestive heart failure and hypertension. There is no predictability, prior to their testing, as to what compositions will or will not be effective in their treatment. U.S. Pat. No. 4,302,464 to LaMattina et al. and in the LeMattina article entitled "The Synthesis of 2-Amino-4-(4-imidazolyl)pyridines" in the *Journal of Heterocyclic Chemistry*, 20, pp. 533–538, 1983, there is a description of 2-substituted-4-(4-imidazolyl)pyridines and their pharmaceutical compositions for their use as anti-ulcer agents. These compositions are not the same compositions as used in the present invention since the LaMattina et al. compositions are not substituted with carboxylic acid and esters thereof on the imidazolyl radical. The LaMattina et al. compositions are satisfactory for controlling gastric acidity and are useful in the treatment of peptic ulcers and the like, but are not known for the treatment of cardiovascular ailments.

Some of the pyridinylimidazole compositions and their methods of preparation used in the present invention, are described in an article entitled "An Efficient Synthesis of 5-Diethoxymethylimidazole-4-Carboxylate, A Potential Precursor For Various Imidazole Derivatives" by Murakami et al. in *Tetrahedron Letters*, Vol. 23, No. 45, pp. 4729–4732, 1982. Murakami et al. describes the preparation of pyridinylimidazole-5-substituted carboxylic acid esters but there is no teaching nor recognition of their uses in treatment of cardiovascular ailments which are described in the present invention.

SUMMARY OF THE INVENTION

It has been discovered that a therapeutically effective amount of pyridinylimidazole 4- or 5-substituted carboxylic acid and esters thereof in a pharmaceutical acceptable carrier are useful for the treatment of cardiovascular ailments such as congestive heart failure and hypertension. The pyridinylimidazole compounds are of the formulae:

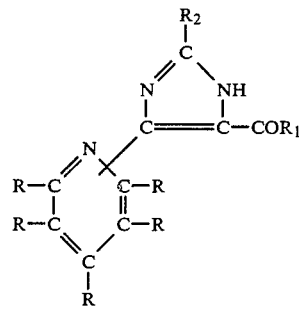

and the pharmaceutically acceptable acid addition salts thereof, where the imidazole radical is substituted on one of the R substituents and each of the remaining R substituents is hydrogen or $R_1$ and each $R_1$ is independently hydroxy, amino, alkylamino, or alkoxy, and $R_2$ is hydrogen, alkyl, halo, or hydroxy; wherein any alkyl radical contains 1 to 6 carbon atoms.

Since N-unsubstituted imidazoles can exist as tautomeric forms as has been well documented (e.g. K. Hofmann, "Imidazole and its Derivatives Part I", Interscience Publishers, Inc.: New York, 1953; pages 3 to 5), the tautomer (shown below) is also included in this invention. The names of the examples in this invention cover both the tautomers.

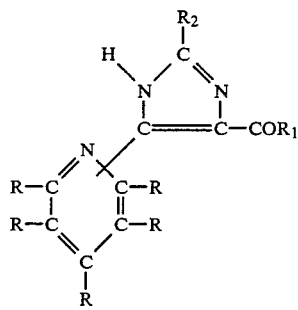

Preferred compounds include
4(5)-(4'-pyridinyl)-imidazole-5(4)-carboxylic acid;
4(5)-(4'-pyridinyl)-imidazole-5(4)-carboxylic acid methyl ester;
4(5)-(4'-pyridinyl)-imidazole-5(4)-carboxylic acid ethyl ester;
4(5)-(2'-pyridinyl)-imidazole-5(4)-carboxylic acid;
4(5)-(2'-pyridinyl)-imidazole-5(4)-carboxylic acid methyl ester;
4(5)-(2'-pyridinyl)-imidazole-5(4)-carboxylic acid ethyl ester;
4(5)-(3'-pyridinyl)-imidazole-5(4)-carboxylic acid;
4(5)-(3'-pyridinyl)-imidazole-5(4)-carboxylic acid methyl ester;
4(5)-(3'-pyridinyl)-imidazole-5(4)-carboxylic acid ethyl ester;
and the like.

The preferred treatment technique is the oral administration of the pharmaceutical composition comprising a pharmaceutically acceptable carrier and a therapeutic amount of the compounds identified in the above defined formulae.

DETAILED DESCRIPTION OF THE INVENTION

The method of preparation of the pyridinylimidazole compounds used in the compositions of this invention are described in the Murakami et al. article discussed in the prior art section. Briefly, cyanopyridines such as 2-cyanopyridine, 3-cyanopyridine or 4-cyanopyridine or alkyl-substituted cyanopyridine, is reacted with an isocyanocarboxylate such as methyl isocyanoacetate, ethyl isocyanoacetate, hexyl isocyanoacetate and the like, in the presence of a base such as sodium hydride or potassium hydride and the like, and a reaction-inert solvent such as diglyme, tetrahydrofuran and the like. The reaction is conducted at temperatures from about 0° C. to about 90° C. for a sufficient period of time such as a few minutes to as many as 24 hours, if necessary, to complete the reaction. The reaction product is quenched with a saturated aqueous ammonium chloride solution, extracted with methylene chloride, and additionally with ethylacetate. The combined organic layer is dried over sodium sulfate and concentrated. The resulting slurry is filtered, the product washed with water and the pyridinylimidazole product recrystallized from methanol.

The pharmaceutically acceptable acid addition salts of the pyridinylimidazole 4- or 5-substituted carboxylic acid or esters thereof used in this invention are prepared by treating the pyridinylimidazole compounds with various mineral and organic acids which form nontoxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by simply using the proper molar amount of the appropriate acid in an aqueous solvent medium or in a suitable organic solvent such as methanol or ethanol. Upon careful evaporation of the solvent, the solid salt is readily obtained.

The pyridinylimidazole 4- or 5-substituted carboxylic acid or esters thereof as used in this invention, are readily adapted to therapeutic use to relieve cardiovascular ailments such as hypertension or congestive heart failure. These results can be achieved when given by the intravenous route of administration at dose levels ranging from about 1 milligram/kilogram to about 100 milligrams/kilograms of bodyweight, without showing any substantial signs of toxic side effects. Additionally, the compositions of the present invention can be administered orally without causing any significant untoward pharmacological side reactions to occur in the subject to whom they are administered. In general, these compositions are ordinarily administered at dosage levels ranging from about 0.5 milligram to about 50 milligrams per kilogram of body weight although variations will necessarily occur depending upon the condition and individual response of the subject being treated and the particular type of pharmaceutical formulation chosen.

The compositions of this invention are administered with pharmaceutically acceptable carriers in both single and multiple dosages. The compositions of this invention can be administered in a wide variety of different dosage forms, i.e., they may be combined with various pharmaceutically acceptable inert carriers in the form of tablets, capsules, lozenges, troches, hard candies, powders, aqueous suspensions, elixirs, syrups, and the like. Such carriers include solid diluents or fillers, sterile aqueous media and various non-toxic organic solvents, etc. Moreover, such standard pharmaceutical compositions can be suitably sweetened and/or flavored by means of various agents of the type commonly employed for such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients, such as sodium citrate, may be employed along with various disintegrants such as starch and preferably potato or tapioca starch, alginic acid and certain complex silicates together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular polyethylene glycols. When aqueous suspensions and/or elixers are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

For purposes of parenteral administration, solutions or suspensions of the instant compositions in sesame or peanut oil or in aqueous propylene glycol solutions can be employed, as well as sterile aqueous solutions. These particular solutions are especially suited for intramuscular and subcutaneous injection purposes. The aqueous solutions dissolved in pure distilled water are also useful for intravenous injection purposes provided that their pH is properly adjusted beforehand. Such isolations should also be suitably buffered, if necessary, and the liquid diluent first rendered isotonic with sufficient saline.

The activity of the composition of the present invention as a treatment of congestive heart failure and hypertension can be determined by their ability to pass two standard tests. For example, if the compositions increase the myocardial contractile force, this is useful in treating congestive heart failure. In another test, if the compositions cause slight to moderate decrease of blood pressure, this is useful in treating hypertension.

The following examples and tests further demonstrate the invention:

EXAMPLE I

4(5)-(4'-pyridinyl)imidazole-5(4)-carboxylic acid ethyl ester was prepared in the following manner: to 42 milliliters of diglyme, 6.9 grams sodium hydride in 50% oil dispersion was added slowly. To the resulting solution maintained in an ice bath, is added dropwise and with stirring, a solution of 15.4 grams ethyl isocyanoacetate and 14 grams 4-cyanopyridine in 40 milliliters of diglyme. After the addition is complete, the resulting combination is stirred for one hour at room temperature and them at 50° C. overnight. The resulting product was cooled to room temperature. To the reaction mixture is added 200 milliliters of a saturated solution (28.5 grams/100 ml) of ammonium chloride. The reaction mixture is then extracted with three 10 ml portions of ethylene chloride and finally with 10 ml of ethyl acetate. The combined organic layer recovered was dried over sodium sulfate, concentrated and filtered. The filtered product is washed with water and recrystallized from methanol. The product, 8.3 grams of 4(5)-(4'-pyridinyl)imidazole-5(4)-carboxylic acid ethyl ester M.P. 214°-217° C. is obtained.

A dihydrochloride salt of 4(5)-(4'-pyridinyl)imidazole-5(4)-carboxylic acid ethyl ester is produced by the reacting of 2 moles of hydrochloric acid to the pyridinylimidazole compound.

TEST PROCEDURES

The dihydrochloride salt of Example I is dissolved in saline for intravenous, intraduodenal, and oral testing.

METHOD FOR THE EVALUATION OF INOTROPIC EFFECTS

Animals

Dogs of either sex weighing between 9-15 kg were fasted overnight and anesthetized with pentobarbital sodium, 35 mg/kg, i.v. (Ganes Chemical, Pennsville, NJ). The anesthetic is supplemented in 7-10 mg/kg bolus doses when pupillary reflexes become evident. The animals are intubated with an endotracheal tube (Rusch, size 8-9F, Arista Surgical, New York, NY) and artificially ventilated with room air using a respirator (Model 6076, Harvard Equipment, Millas, MA). The pump volume is adjusted using a standard canine ventilation nonogram which is based on body weight (Harvard Equipment). Each dog is surgically prepared for the acute measurements of arterial blood pressure, heart rate and direct measurement of myocardial contractile force (Walton-Brodie strain gauge).

Arterial Blood Pressure Measurements

Pulsatile arterial pressure is monitored via a polyethylene catheter (PE 240, Clay-Adams, Parsippany, NJ) filled with 0.9% NaCl (Abbott Labs., North Chicago, IL) containing 1 mg/ml heparin (Chemical Dynamics Corp., South Plainfield, NJ), inserted into the right femoral artery via an incision. The tip is advanced until a distinct dicrotic notch is observed on the arterial pressure wave. The catheter is connected to a pressure transducer (P 23 ID, Statham, Oxnard, CA) and a DC Driver Amplifier (Model 7D, Grass Instruments, Quincy, MA). Mean arterial pressure is determined electronically by damping the pulsatile pressure signal. The output of the transducer amplifier is displayed on one channel of a strip chart recorder (Model 7D, Grass Instruments). The catheter is calibrated ex vivo using a mercury manometer prior to introduction into the femoral artery.

Heart Rate Measurements

Heart rate is monitored by a Tachometer Preamplifier (7 P4, Grass Instruments) coupled to the pulsatile arterial pressure DC Driver Amplifier (Grass Instruments). The output of the tachometer is displayed on the strip chart recorder (Grass Instruments).

Myocardial Contractile Force Measurements

Myocardial contractile force generated by the left ventricle is directly assessed using a Walton-Brodie strain gauge arch with a movable foot (J. A. Warren, Charleston, SC). A 23 mm working length between foot centers is used. The output of the transducer amplifier is coupled through a D.C. Amplifier (Model 7DAF, Grass Instrument), and displayed on one channel of the recorder.

The arch is calibrated just prior to mounting on the ventricular myocardium. The sliding foot is removed from the casing and the casing clamped in a vertical position with the fixed foot upward. Calibration is performed by suspending calibrated weights from the upper sensitive foot and noting the corresponding pen deflection. The arch is used to record force which is expressed as of grams of developed tension.

The heart is exposed via a left thoracotomy at the level of the 4th or 5th intercostal space. The lungs are carefully retracted with gauze moistened with normal saline. The pericardial sac is then opened broadly while care is taken to avoid major sac vessels. The left anterior descending (LAD) coronary artery is identified and the arch is placed on the ventricular myocardium distal to the 1st major LAD branch and parallel to the LAD itself. The arch is physically attached to the myocardium using braided sutures (Ethicon 1; Somerville, NJ) placed about 16 mm apart. The sutures were placed in the ventricular muscle with a non-cutting edge, half-circle needle; suture depth is approximately 3-5 mm. In placing sutures, care is taken to avoid penetration of the inner chamber and to avoid constriction of any visible coronary vessels. The sutures are then threaded through holes in each of the arch feet and securely tied. The sliding foot is moved to stretch the ventricular muscle segment under the arch by approximately 30-50% of its diastolic length. The pericardial sac is then sewn closed. The strain gauge wires are externalized and the chest is closed.

DRUG ADMINISTRATION

Intravenous Route

Test compounds are administered intravenously via a polyethylene cannula introduced into a femoral vein. The test compounds are injected manually from 5 ml plastic syringes over a 1-3 minute period and the cannula flushed with 1 ml 0.9% NaCl.

Intraduodenal Route

Test compounds are administered introduodenally via a polyethylene cannula inserted into the stomach. The stomach is exposed via a mid-line incision made in the ventral xiphoid region 2 cm below the diaphragm. A purse-string suture is place in the stomach 2-4 cm distal to the pyloric sphincter with a cutting edge, half circle needle. The suture depth is approximately 2-4 mm. A stab wound is then made in the stomach and a polyethylene catheter (PE 200, Clay Adams) advanced 10 cm through the pyloric sphincter into the duodenum. The suture is drawn closed and tied holding the catheter in place.

PROTOCOL

After a 30-45 minute equilibration period, each dog is administered isoproterenol (dl-isoproterenol HCl: Sigma Chemical, St. Louis, MO) in ascending doses of 0.03, 0.1 and 0.3 ug/kg, i.v. in a constant volume of 1 ml. The maximum effect on mean arterial pressure, heart rate and contractile force is measured. Only dogs that have arterial pressures between 80 and 125 mm Hg, heart rates between 110 and 170 bpm and contractile force responses to isoproterenol (0.3 ug/kg, i.v.) between 75 and 160% are utilized. The dog preparation is allowed to re-equilibrate for at least twenty minutes, following the last dose of isoproterenol. Two pretreatment control readings, five minutes apart, are taken followed by the administration of the test compound. The effects of the test compound on mean arterial pressure, heart rate and contractile force are monitored for thirty minutes in one minute intervals for the first five minutes and at five minute intervals thereafter, after each ascending dose of the test compound.

In general, 0.1-10 mg/kg of test compound are administered intravenously and doses up to 300 mg/kg are administered intraduodenally.

DRUG ANALYSIS

The contractile force, mean arterial pressure and heart rate responses for each dog are plotted against the time course of the experiment. The maximum charges are recorded and expressed as a percent of the pretreatment control values.

The following results in Tables I, II and III below were obtained with the saline solution of the dihydrochloride salt of Example I.

TABLE I

Inotropic test intravenously fed (into a femoral vein)

| Dose mg/kg body weight | Maximum Change (% Control) | | |
|---|---|---|---|
| | Contractible Force | Heart Rate | Mean Arterial Pressure |
| 0.1 | −18/9 | 3/7 | 4/−14 |
| 1.0 | 15/25 | 3/11 | −12/−30 |
| 10.0 | 221/89 | 26/33 | −48/−58 |

TABLE II

Inotropic test intraduodenally (via a cannula into the pyloric portion of the stomach)

| Dose mg/kg | Maximum Change (% Control) | | |
|---|---|---|---|
| | Contractible Force | Heart Rate | Mean Arterial Pressure |
| 10 | 38/46 | 18/18 | −8/−5 |
| 30 | 46/52 | 32/18 | −15/−9 |
| 100 | 15/20 | −6/−10 | −34/−40 |

TABLE III

Inotropic test via mouth (oral activity)

| Dose mg/kg | Maximum Change (% Control) | | |
|---|---|---|---|
| | Contractible Force | Heart Rate | Mean Arterial Pressure |
| 10 | 29/−18 | 15/7 | 39/21 |
| 30 | 56/56* | 24/35* | −39/50* |

*This dog became very excited and the experiment was terminated.

As indicated in the above tables the dihydrochloride salt of 4(5)-(4'-pyridinyl)imidazole-5(4)-carboxylic acid ethyl ester consistently increases the myocardial contractile force; thus it is very useful for the treatment of congestive heart failure. The oral activity makes the treatment more convenient especially for outpatients. Also demonstrated in Tables I and II, the dihydrochloride salt of Example I caused slight to moderate decrease of blood pressure. Since many congestive heart failure patients also have hypertensive conditions, this blood pressure lowering effect can be an added benefit to them. The increase in heart rate in all tests at doses 10 mg/kg or less is minimal. At higher doses, the results are variable. There were no apparent adverse effects in the intravenous and intraduodenally tests. In the oral administration test, one of the two dogs developed excitment and had to be sacrificed. Since only two dogs were used in this test, the significance of this undesired effect is unclear at the present time.

What is claimed is:

1. A pharmaceutical composition useful for treatment of congestive heart failure and hypertension comprising a pharmaceutically acceptable carrier and a therapeutically effective amount of a compound selected from the group consisting of pyridinylimidazoles of the formulae:

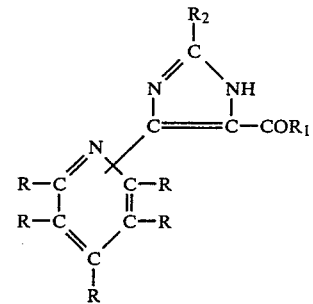

and pharmaceutically acceptable acid addition salts thereof,
wherein the imidazole radical is substituted on one of the R substituents and each of the remaining R substituents is hydrogen,
$R_1$ is hydroxy, amino, methoxy or ethoxy, and
$R_2$ is hydrogen, halo, or hydroxy.

2. The composition of claim 1 wherein the pyridinylimidazole is 4(5)-(4'-pyridinyl)imidazole-5(4)-carboxylic acid ethyl ester.

3. The composition of claim 1 wherein the pyridinylimidazole is 4(5)-(4'-pyridinyl)imidazole-5(4)-carboyxlic acid methyl ester.

4. The pharmaceutical composition of claim 1 in the form of an oral composition.

5. The pharmaceutical composition of claim 1 in the form of an intravenous composition.

* * * * *